(12) United States Patent
Schmidt et al.

(10) Patent No.: US 10,376,217 B2
(45) Date of Patent: Aug. 13, 2019

(54) POSITIONING UNIT FOR POSITIONING A PATENT, IMAGING DEVICE AND METHOD FOR THE OPTICAL GENERATION OF A POSITIONING AID

(71) Applicant: Siemens Aktiengesellschaft, Munich (DE)

(72) Inventors: Bernhard Schmidt, Fuerth (DE); Martin Sedlmair, Zirndorf (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 681 days.

(21) Appl. No.: 14/661,502

(22) Filed: Mar. 18, 2015

(65) Prior Publication Data

US 2015/0272505 A1 Oct. 1, 2015

(30) Foreign Application Priority Data

Mar. 27, 2014 (DE) ........................ 10 2014 205 702

(51) Int. Cl.
*A61B 5/055* (2006.01)
*A61B 5/00* (2006.01)
(Continued)

(52) U.S. Cl.
CPC ............ *A61B 5/706* (2013.01); *A61B 5/0555* (2013.01); *A61B 6/032* (2013.01); *A61B 6/035* (2013.01);
(Continued)

(58) Field of Classification Search
CPC ....... A61B 5/0555; A61B 5/706; A61B 6/032; A61B 6/035; A61B 6/0492; A61B 6/102; A61B 6/4014; A61B 6/54; A61B 6/547
See application file for complete search history.

(56) References Cited

U.S. PATENT DOCUMENTS 5,572,568 A 11/1996 Kanemitsu
2007/0189456 A1 8/2007 Haras
(Continued)

FOREIGN PATENT DOCUMENTS

CN 1915171 A 2/2007
CN 101036584 A 9/2007
(Continued)

OTHER PUBLICATIONS

Korean Office Action and English translation thereof dated Apr. 20, 2016.
(Continued)

*Primary Examiner* — Mark D Remaly
(74) *Attorney, Agent, or Firm* — Harness, Dickey & Pierce, P.L.C.

(57) ABSTRACT

A positioning unit includes a projector and a control unit and enables a particularly quick and precise positioning of a patient. In an embodiment, the control unit affects a control of the projector as a function of a protocol for a recording of an image of the patient such that the positioning unit is designed for the planar projection of a figure as a positioning aid on the patient couch. An immediately apparent area on the patient couch is then specified by the figure projected in a planar fashion, relative to which the patient can be positioned. The control unit can be used both to temporally control the projection process and also to control the figurative properties of the positioning aid. Furthermore, the control unit can include a device for calculating a control signal so that the control unit brings about control of the projector with the control signal.

11 Claims, 5 Drawing Sheets

(51) Int. Cl.
*A61B 6/03* (2006.01)
*A61B 6/04* (2006.01)
*A61B 6/00* (2006.01)
*A61B 6/10* (2006.01)

(52) U.S. Cl.
CPC .............. *A61B 6/0492* (2013.01); *A61B 6/54* (2013.01); *A61B 6/102* (2013.01); *A61B 6/4014* (2013.01); *A61B 6/547* (2013.01)

(56) References Cited

U.S. PATENT DOCUMENTS

| | | | |
|---|---|---|---|
| 2009/0147224 A1 | 6/2009 | Kurozuka et al. | |
| 2009/0180590 A1 | 7/2009 | Borgmann et al. | |
| 2011/0135190 A1 | 6/2011 | Maad | |
| 2015/0208989 A1 | 7/2015 | Rackow et al. | |
| 2015/0272505 A1 | 10/2015 | Schmidt et al. | |
| 2015/0305597 A1* | 10/2015 | Ito | G02B 23/26 600/424 |

FOREIGN PATENT DOCUMENTS

| | | |
|---|---|---|
| CN | 101268402 A | 9/2008 |
| CN | 102193287 A | 9/2008 |
| CN | 101472523 A | 7/2009 |
| CN | 102090899 A | 6/2011 |
| CN | 102525524 B | 11/2013 |
| DE | 102012216850 B3 | 2/2014 |
| JP | H07327984 A | 12/1995 |
| JP | 2013025014 A | 2/2013 |
| KR | 20060017189 A | 2/2006 |
| WO | WO 2009011643 A1 | 1/2009 |
| WO | WO 2011071442 A1 | 6/2011 |
| WO | WO 2013072872 A1 | 5/2013 |

OTHER PUBLICATIONS

Krauss, Bernhard: "Bone Removal and Dual Energy CT", in: Internal Communication, pp. 1-8; Aug. 12, 2005.
Krauss, Bernhard: "Material Decomposition & Dual Energy", in: Internal Communication, pp. 1-11; Aug. 8, 2005.
Kraus, Bernhard: "Contrast Enhancement and Dual Energy CT", in: Internal Communication, pp. 1-7; Jul. 15, 2005.
German Office Action dated Feb. 4, 2015.
Chinese Office Action and English translation thereof dated Dec. 5, 2016.
Korean Office Action dated Oct. 4, 2016.
Chinese Office Action and English translation thereof dated Mar. 28, 2018.
Office Action for Chinese Patent Application No. 201510140835.1 dated Oct. 18, 2018 and English translation thereof.

* cited by examiner

POSITIONING UNIT FOR POSITIONING A PATENT, IMAGING DEVICE AND METHOD FOR THE OPTICAL GENERATION OF A POSITIONING AID

PRIORITY STATEMENT

The present application hereby claims priority under 35 U.S.C. § 119 to German patent application number DE 102014205702.7 filed Mar. 27, 2014, the entire contents of which are hereby incorporated herein by reference.

FIELD

At least one embodiment of the invention is directed to a positioning unit for positioning a patient, imaging device and/or a method for the optical generation of a positioning aid.

BACKGROUND

In medical imaging, increasingly greater temporal and spatial resolutions are achieved. It is therefore possible in magnetic resonance tomography and computed tomography to record high resolution, spatial three-dimensional images of a moving recording area such as for instance the beating heart of a patient. In order for the technically possible resolution also actually to be achievable, the patient must be positioned accordingly on a patient couch. Furthermore, it is also desirable for as quick and low-radiation a recording as possible to position the patient according to the requirements of a specific protocol or a specific medical question.

The positioning of a patient can be assisted using laser light, whereby a laser projects a line onto the patient couch or the patient. For instance, the companies LAP Laser and Laser Components manufacture appropriate lasers. While the positioning with lasers is largely suited to specifying injection sites for an intervention or tissue to be irradiated during radiation therapy, such a positioning for recording a tomographic image only offers a restricted functionality. Therefore the conventional positioning by means of a laser does not take the orientation and precise support position of the patient into account. Furthermore, a positioning in daily clinical practice is to take place quickly and as accurately and in as non error-prone a fashion as possible.

Furthermore, it may be that the patient was basically positioned correctly, but on account of various restrictions of the imaging device, no recording with the selected protocol and the respective positioning is possible. An example here may be a recording as a "Flash-Spiral" with the computed tomograph Somatom Definition Flash by Siemens, in which the patient couch is advanced so quickly that specific travelling times and directions are required. As a result the available area of the patient couch is restricted for a support of the area of the patient to be recorded.

The position of the patient can be controlled by use of a topogram. A topogram is an overview image for planning a further, higher-quality recording. Such an overview image is generally not resolved in a spatial three-dimensional fashion. The recording of a topogram is also associated with radiation exposure to the patient. Unnecessary and repeated recordings of topograms are therefore to be avoided. The recording of a topogram, which, in computed tomography, is also used to calculate parameters for dose modulation during a further tomographical recording, is therefore to already take place in precisely the positioning of the patient, in which the tomographic recording is to be performed.

SUMMARY

At least one embodiment of the present invention is directed to enabling a quick, accurate and less error-prone positioning of a patient on a patient couch. It is further desirable for different protocols and support positions of the patient to be simultaneously assisted during the positioning process.

At least one embodiment of the present invention is directed to a positioning unit, an imaging device and a method.

Features, advantages or alternative embodiments mentioned here are similarly also transferred to other claimed subject matters and vice versa. In other words, the claims in question (which focus on an x-ray device for instance) can also be further developed with the features, which are described or claimed in conjunction with a method. The corresponding functional features of the method are in this way embodied by corresponding modules in question.

In an embodiment, inventors have identified that a positioning unit with a projector and a control unit then enables a particularly quick and at the same time accurate positioning if the control unit brings about a control of the projector as a function of a protocol for a recording of an image of the patient, such that the positioning unit is designed for the planar projection of a figure as a positioning aid on the patient couch. The figure projected in a planar fashion then specifies an immediately apparent region on the patient couch, relative to which the patient can be positioned. The control unit can be used both to temporally control the projection process and also to control the figurative properties of the positioning aid. The combination of the rapidly detectable planar projection of a figure with the dependency of the control of the projection on the protocol finally results in a positioning of the patient which is only prone to errors to a limited degree.

At least one embodiment of the invention can be embodied both as a positioning apparatus as described previously and also as an imaging device with such a positioning apparatus.

According to the cited variants and aspects, at least one embodiment of the invention can be embodied as methods with the respectively cited advantages. At least one embodiment of the inventive method is based here on the planar projection of a figure as a positioning aid such that the figure for positioning a patient is suited to recording an image of the patient. Furthermore, the figure can be projected in a planar fashion onto the patient couch as a function of a protocol for a recording.

In further developments of at least one embodiment of the invention, the previously cited aspects and variants can also relate to the recording of a tomographic image of the patient and thus also to a protocol for a recording of a tomographic image of the patient.

BRIEF DESCRIPTION OF THE DRAWINGS

The invention is described and explained in more detail with the aid of the example embodiments shown in the figures, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In an embodiment, inventors have identified that a positioning unit with a projector and a control unit then enables a particularly quick and at the same time accurate positioning if the control unit brings about a control of the projector as a function of a protocol for a recording of an image of the patient, such that the positioning unit is designed for the planar projection of a figure as a positioning aid on the patient couch. The figure projected in a planar fashion then specifies an immediately apparent region on the patient couch, relative to which the patient can be positioned. The control unit can be used both to temporally control the projection process and also to control the figurative properties of the positioning aid. The combination of the rapidly detectable planar projection of a figure with the dependency of the control of the projection on the protocol finally results in a positioning of the patient which is only prone to errors to a limited degree.

The invention, in at least one embodiment, provides an even more flexibly adjustable solution, if the positioning unit is designed for the planar projection of the figure in the form of a schematic representation of a human body in different support positions. The projected figure of a schematic representation of a human body is to be used to determine how precisely the patient is to be positioned. The patient is simply positioned according to the projected figure on the patient couch. A particularly flexible positioning is consequently already provided by the possibility of the schematic representation in different support positions such that the invention allows for adjustment to a plurality of different usage scenarios. A positioning can consequently take place particularly accurately so that the patient, when being supported on the patient couch, is aligned with the projected figure such that the posture of the patient is adjusted to a posture which is prespecified by the figure.

According to a further aspect of at least one embodiment of the invention, the positioning unit is designed for the planar projection of the figure in various sizes, based on a scalable model. The positioning is even quicker and more precise on account of an adjustment of the size of the figure.

In a further variant of at least one embodiment of the invention, the planar projection takes place as a function of a retrievable, stored set of patient data. The control unit is then designed to obtain parameter values for the scalable model from the retrievable stored set of patient data. This enables as quick and technically reliable an implementation as possible of the adjustment of the scalable model to the properties of the patient to be positioned.

According to a further aspect of at least one embodiment of the invention, the positioning unit is designed for the planar projection of a first symbol in order to indicate a direction of the recording. As a result the positioning of the patient is above all enabled with lower susceptibility to errors.

According to a further aspect of at least one embodiment of the invention, the positioning unit is designed for the planar projection of a second symbol in order to indicate the recording area. The additional information of the recording area further reduces the probability of a faulty positioning of the patient.

Furthermore, the control unit may comprise at least one device for calculating a control signal, so that the control unit brings about the control of the projector with the control signal. Furthermore, the at least one device for calculating can be configured specifically such that they set up the positioning unit to realize at least one embodiment of the invention according to the afore-cited aspects and variants. The control unit can therefore be designed to send the control signal. Furthermore, the projector can be designed to receive and process the control signal. The control unit is then also designed to transmit a control signal to the projector as a function of a protocol for the recording of an image of the patient, so that a plurality of parameters, which define the protocol, can be taken into account in the planar projection.

According to a further aspect of at least one embodiment of the invention, the positioning unit has at least one device for controlling the position of the patient couch so that the positioning unit is embodied for the planar projection of the figure at a specific position relative to the patient couch. This aspect of at least one embodiment of the invention is particularly advantageous, because it ensures that sufficient directions are enabled for a rapid acceleration of the patient couch.

According to a further aspect of at least one embodiment of the invention, the projector is positioned centrally above the patient couch. As a result, the projection takes place in as distortion-free a fashion as possible.

At least one embodiment of the invention can be embodied both as a positioning apparatus as described previously and also as an imaging device with such a positioning apparatus.

According to the cited variants and aspects, at least one embodiment of the invention can be embodied as methods with the respectively cited advantages. At least one embodiment of the inventive method is based here on the planar projection of a figure as a positioning aid such that the figure for positioning a patient is suited to recording an image of the patient. Furthermore, the figure can be projected in a planar fashion onto the patient couch as a function of a protocol for a recording.

In further developments of at least one embodiment of the invention, the previously cited aspects and variants can also relate to the recording of a tomographic image of the patient and thus also to a protocol for a recording of a tomographic image of the patient.

Figure 1:
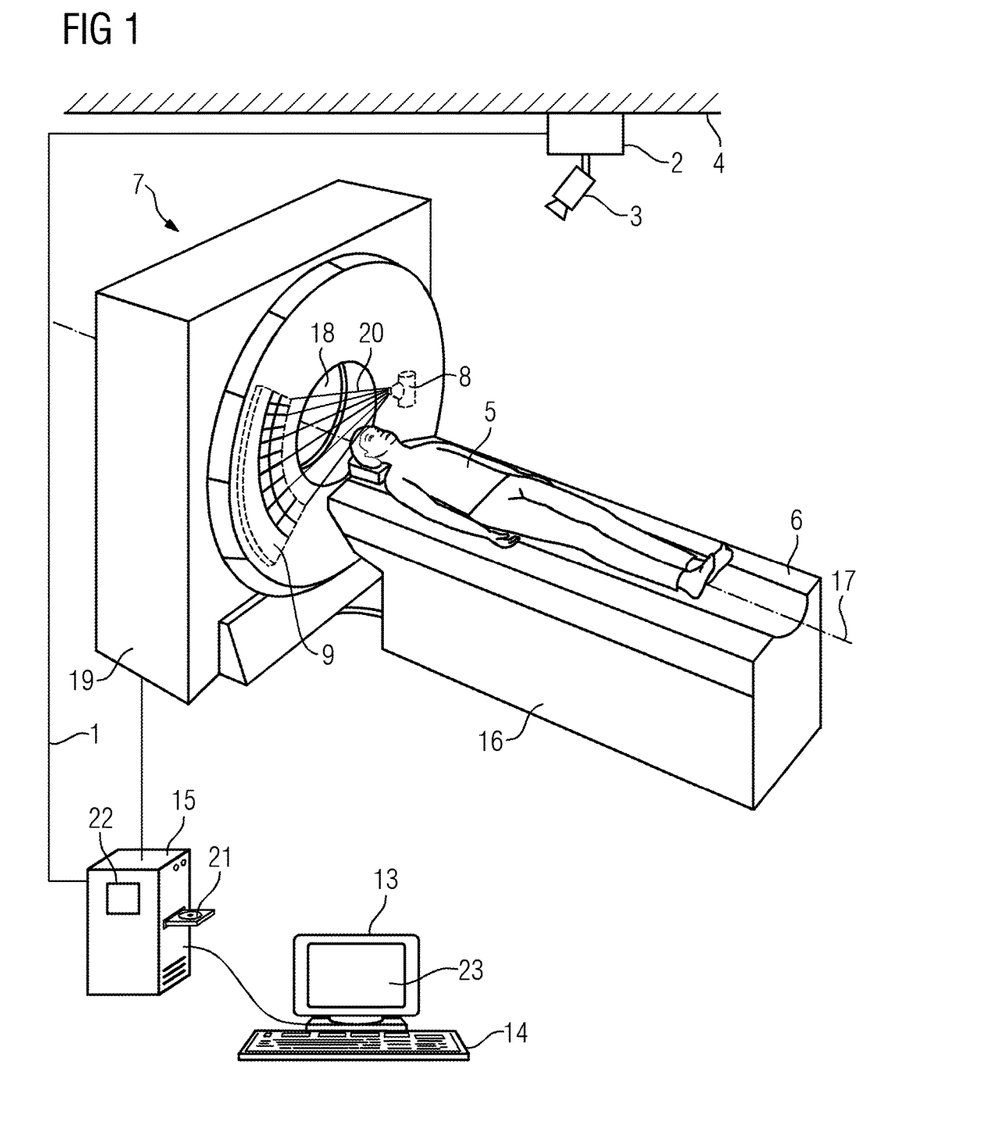
FIG. 1 shows an inventive imaging device in the form of a computed tomography system.

FIG. 1 shows an inventive imaging device in the form of a computed tomography system. A tomographic recording is a recording of a spatial three-dimensional image, which in particular allows for the generation of individual sectional images of the patient 5. With the recording of a tomographic image, the patient 5 is on a patient couch 6, which is connected to a couch base 16, such that it supports the patient couch 6 with the patient 5. With a tomographic recording, a spatial three-dimensional scanning takes place of the patient 5 supported on the patient couch 6. Such a scanning can be effected in particular by a relative movement of the patient 5 and a recording unit. Depending on the imaging device 7, the patient couch 6 can be moved both with the patient 5 or the recording unit.

In the example shown here, during a tomographic recording the patient couch 6 is moved along a system axis 17 through the opening 18 of the gantry 19 of the computed tomography system. During this movement, a plurality of x-ray projections of the area of the patient 5 to be recorded is recorded. Spatial three-dimensional x-ray images, in particular sectional images, can be reconstructed from these x-ray projections. During the tomographic recording of an x-ray image, in the instance shown here, the recording unit rotates with an x-ray detector 9 and with an x-ray emitter 8, which interacts with the x-ray detector 9, about the system axis 17. The x-ray emitter 8 and x-ray detector 9 are arranged in a gantry 19 such that they face one another and the x-rays 20 of the x-ray emitter 8 can be detected for the x-ray detector 9. In the example shown here, the x-ray emitter 8 is an x-ray tube and the x-ray detector 9 is a detector with a number of rows and columns.

In a further embodiment, the computed tomography system has in each instance two pairs of x-ray emitters 8 and x-ray detectors 9 which interact with one another such that the computed tomography system is particularly suited to multi-energy recordings. In an alternative embodiment (not shown here), the imaging device 7 is a C-arm x-ray device. With a C-arm x-ray device, other types of x-ray emitter 8 and x-ray detectors 9 can be used in particular. For instance, a planar detector can be used as an x-ray detector 9. In further embodiments, the imaging device 7 is a magnetic resonance tomograph, in which a magnet is used to generate radiation and a coil is used to detect radiation.

Furthermore, the imaging device 7 can be connected to a computer 15 or include the same. The computer 15 can be designed to control the imaging device 7, in particular to select a protocol for a recording of an image. In the example shown here, the computer 15 has a control unit 22 for generating a control signal 1. The means for calculating a control signal 1 can be embodied both in the form of hardware and also software. An interface allows the control unit 22 to communicate with the projector 3. The control unit 22 or the computer 15 has further interfaces, in the embodiment shown here, in order to be able to communicate with the input unit 4 or an output unit 13. The interfaces are generally known hardware or software interfaces, e.g. hardware interfaces PCI bus, USB or fire wire. The transmission of the control signal 1 from the control unit 22 to the projector 3 can take place in both a wired and also wireless fashion.

The computer 15 is designed to load a computer program into its internal memory, wherein the computer program includes commands which can be read by the computer 15. The commands of the computer program which can be read by the computer 15 are designed to control embodiments of the inventive method if the commands are executed on the computer 15. In further embodiments of the invention, both the computer program and also the control unit 22 are designed to access a protocol 10 for a recording of an image on a scalable model 11 and to access patient data 12 and to calculate the control signal 1 and to control the projector 3 and the projection process. Furthermore, the computer program can be stored on a machine-readable medium 21. The machine-readable medium 21 may also be a DVD, a USB stick a hard disk or a floppy disk for instance.

The computer 15 is connected to an output unit 13, for instance for the graphic output 23 of tomographic images. The output unit 13 is for instance one (or several) LCD, plasma or OLED monitor(s). Furthermore, the computer 15 is connected to an input unit 4. The input unit 4 is used for instance to select a protocol 10 for the recording of an image of the patient 5 or to confirm the positioning of the patient 5 or the patient couch 6 by a mouse click or to start the recording of the image. The input unit 14 is for instance a keyboard, a mouse, a so-called touchscreen or also a microphone for speech input.

An embodiment of the inventive positioning aid and an embodiment of the inventive imaging device 7 are configured such that they execute embodiments of the inventive method steps and/or can actuate the devices which correspond to performing embodiments of the inventive method. In particular, patient data 12 can be stored on a second computer and retrieved in the internal memory of the first computer 15 by way of a network connection. The second computer is for instance a radiology information system, in brief RIS, on which a plurality of patient data 12, in particular the age or sex of the patient 5, can be stored.

An embodiment of the inventive positioning unit for positioning a patient 5 further includes a projector 3. The positioning unit is designed for the planar projection of a figure as a positioning aid on the patient couch 6 via the projector 3 and via the control unit 22. The projection is a projection of the light generated by the projector 3. A projector 3 is designed to generate light, in other words electromagnetic radiation in the visible spectral range. For instance, the projector 3 can generate light by means of a bulb, a halogen lamp, a diode or a laser. In this way the projector 3 can be embodied as a scanner, which generates a planar projection by rapidly scanning the projection surface with a light spot or light line. Rapidly here means that the scanning process is not perceivable to the human eye. The projector 3 can however also generate a static projection without the scanning process. Furthermore, a projector 3 typically comprises optical elements such as lenses for generating the projection. Furthermore, a projector 3 has a signal processing unit for generating a projection in accordance with the control signal 1. The signal processing unit can be embodied both in the form of hardware and also software.

A projection is planar within the meaning of the present application, if it appears to be flat to the human eye. Therefore, an individual, straight line, as is used conventionally for instance to position a patient 5 in the computer tomgraph, is not considered to be planar. By contrast, a curved line, which encloses a surface, can be considered to be planar, since the enclosed surface appears to be two-dimensional. In particular, a planar projection is provided, if the aspect ratio, in other words the ratio between the length and width of the projection or the surface enclosed by the projection, is less than 1:10, in other words for instance 1:2, 1:3 or 1:4. A planar projection is then also provided if the projection takes place on a surface which is curved in the three-dimensional space. Therefore a patient couch 6 and/or the surface of the patient 5 is generally not flat, but instead curved and structured.

Within the meaning of the present application, a figure is a clearly bordered surface, in other words a surface with a clearly recognizable contour. In particular a figure can be a geometric form or a symbol 24 such as an arrow or the schematic representation of a human body. Such a figure is projected in accordance with the invention onto the patient couch 6. This also includes the situation in which the patient 5 is supported or positioned on the patient couch 6, so that the figure is projected at least partially onto the patient 5. The projection takes place such that the projection not only comprises specific properties such as shape, brightness, contrast or color, but also has a specific position relative to the patient couch 6. The position relative to the patient couch 6 is influenced for instance by the angle of the projection or the position of the patient couch 6. The control signal 1 therefore relates to both the generation of the projection with respect to properties such as shape, brightness, contrast or color and also to the position of the projection relative to the patient couch 6. For instance, the control unit 22 can calculate the position and thus the proportions of the control signal 1, which relate to the position of the projection, with the aid of patient data 12, a protocol 10, the current or a predetermined position of the patient couch 6.

The positioning unit can be designed to acquire the position of the patient couch 6, for instance by acquiring a corresponding position signal. In a variant of an embodiment of the invention, the control unit 22 is designed to acquire and process such a position signal. The control unit 22 can then determine the projection of the figure and in particular the position of the figure as a function of the position of the patient couch 6. Furthermore, the positioning unit can comprise at least one device for controlling the position of the patient couch 6, so that the figure is projected at a specific position relative to the patient couch 6, in particular relative to a periphery or an edge of the support surface of the patient couch 6. For instance, the at least one device for controlling can be the already described control unit 22 or a further signal processing unit. A corresponding control unit 22 or a signal unit is designed to calculate a reclining signal, wherein the reclining signal is used to control the position of the patient couch 6. A control unit 22 or signal unit thus has means for calculating in the form of hardware or software. Furthermore, a corresponding control unit 22 or signal unit has an interface for communicating with the patient couch 6, in particular in order to send the reclining signal to the patient couch 6 and thus to effect a control of the position of the patient couch 6.

A protocol 10 for a recording of an image includes recording parameters such as for instance the recording area, the reclining speed, or parameters for actuating the x-ray source such as the strength or duration of the irradiation. The protocol 10 can also include the temporal spacings of individual recordings or the point in time of the recording relative to a specific point in time, for instance the up-take of a contrast agent. A protocol 10 and the corresponding recording parameters can be predefined for a specific type of recording such as for instance the already cited "flash scan". A protocol 10 and the corresponding recording parameters can be modified in variants of the invention but also however individually. For a specific protocol 10, in particular in conjunction with individual patient data 12, specific requirements are placed on the positioning of the patient 4. The invention allows for an individual and precise adjustment of a positioning aid to these requirements so that the positioning takes place in a rapid and reliable fashion.

In particular, the projection of the figure and its position and the positioning of the patient couch 6 can be made dependent on the planned movement of individual components of the imaging device 7. For instance, a positioning may be desired such that a collision of the patient 5 with a robot arm or a C-arm is avoided. Furthermore, the invention can include the projection of a symbol 24, which specifies danger areas. The invention herewith enables a particularly reliable positioning of the patient 5.

A projected figure is suitable as a positioning aid, if it specifies the position in which the patient 5 is to be supported for the recording of an image on the patient couch 6. The positioning aid can therefore relate both to the orientation of the patient 5 within the meaning of face-down, dorsal or side position and also the absolute position of the patient 5. Furthermore, the projection can mark the position of the area to be recorded, for instance by specifying a surface upon which the region to be recorded is to be placed. Furthermore, the projection can also relate to information relating to the region to be recorded itself. For instance, the projection may have the form of a certain organ or body part of the patient 5 to be recorded. Furthermore, the projection can also correspond to a human representation 25, with which the patient 5 is to be aligned. In this way the control signal 1 can relate in particular to information relating to the position of individual body parts to be projected.

Figure 2:
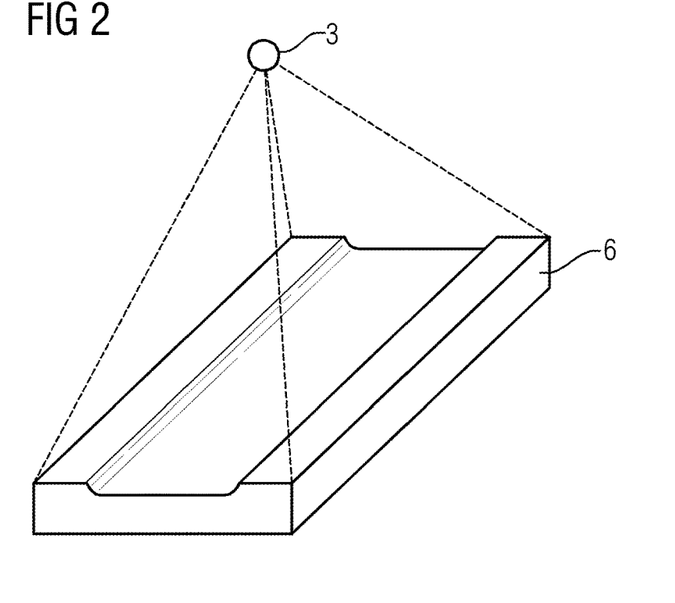
FIG. 2 shows a centrally arranged projector.

In order to generate such a projection, the projector 3 must be positioned accordingly. In the example shown in FIG. 1, the projector 3 is fastened to the ceiling 4 of a room by means of a support 2. In further embodiments, the projector can however also be fastened to the wall of a room or on a separate frame or on the imaging device 7 itself. The projector 3 is advantageously positioned and fastened such that the geometric distortions of the projection are as low as possible. In particular, the projector can be fastened, as shown in FIG. 2, centrally above the patient couch 6. In this way the dashed lines specify the projection area of the projector 3. Centrally here means that the projector 3 is located centrally above the patient couch 6 both in respect of the longitudinal axis and also the transverse axis.

Figure 3:
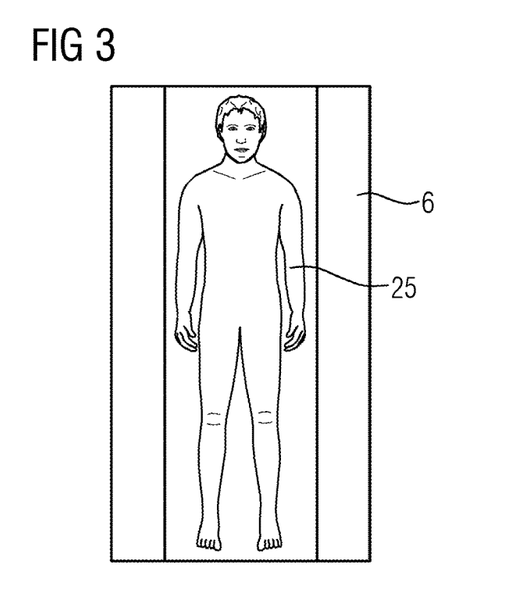
FIG. 3 shows an example projection of a figure in the form of a schematic representation.
Figure 4:
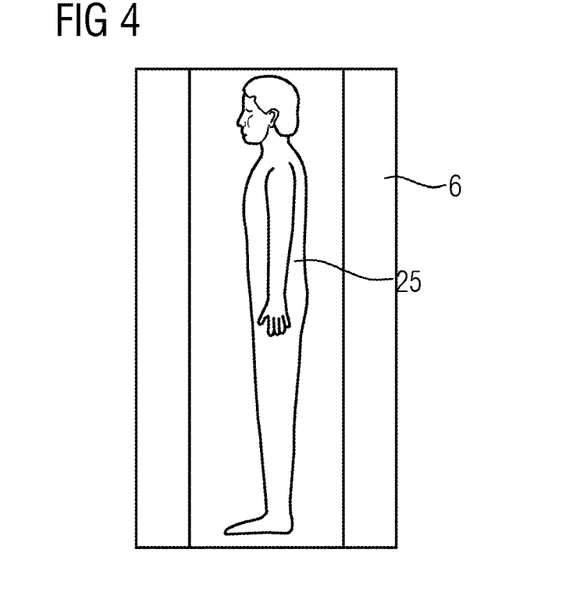
FIG. 4 shows an example projection of a figure in the form of a schematic representation.

FIG. 3 and FIG. 4 each show by way of example a projection of a figure in the form of a schematic representation of a human body, wherein the support position of the figure differs in each instance. FIG. 3 is used as a positioning aid, which specifies that the patient 5 is to be supported on his/her back. FIG. 4 shows a positioning aid which specifies a support position in the side position. Furthermore, it is apparent in both variants that the contour of the figure is clearly recognized and the patient 5 can therefore be positioned according to the figure shown. In further embodiments of the invention, the projected figure, in particular in the form of a schematic representation 25 of a human body, can relate to a scalable model 11. Such a scalable model 11 can be stored in a retrievable fashion for instance on a computer 15 or directly in the control unit 22. Specific properties of the figure are fixedly predetermined in a scalable model 11, whereas other properties can be scaled by certain parameter values being take into account. For instance, the scalable model 11 can be the contour of a human representation 25 or the contour of individual body parts of a human. Properties such as the size, the diameter of the ribcage or the shoulder width can then be adjusted. Such an adjustment takes place in one embodiment according to patient data 12 stored in a retrievable fashion. The patient data 12 relates for instance to the size, the weight, cardiological values or the sex of the patient 5. The patient data 12 can also be measured directly prior to or even during the projection.

Figure 5:
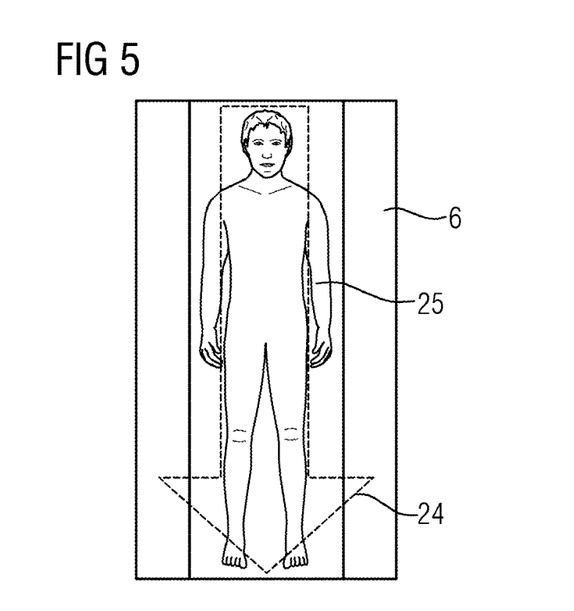
FIG. 5 shows an example projection of a figure specifying the scan direction.
Figure 6:
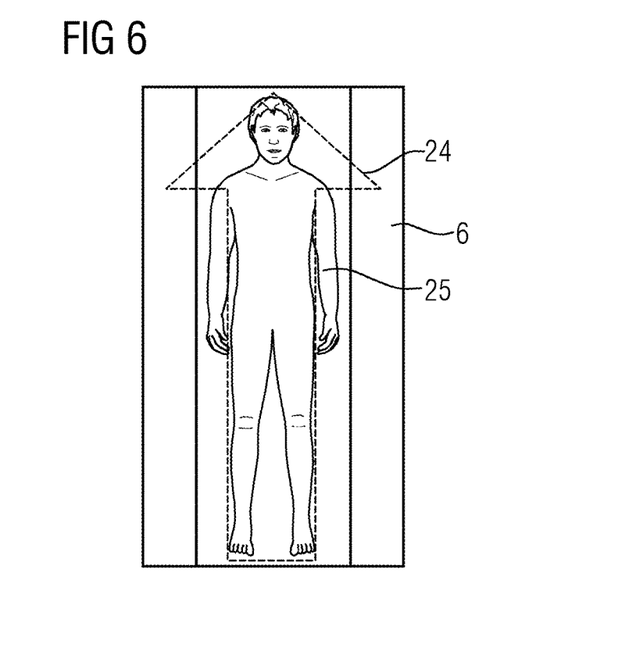
FIG. 6 shows an example projection of a figure specifying the scan direction.

FIG. 5 and FIG. 6 show in each instance an example projection of a figure specifying the scan direction. In the examples shown here, a symbol 24 is, in addition to the figure according to a human representation 25, shown in the form of an arrow on the patient couch 6, wherein the arrow in each case indicates the scan direction of a recording. In particular the scan direction of a recording of a tomographic image can be shown. The scan direction shown in FIG. 5 is also referred to as craniocaudal, whereas the scan direction shown in FIG. 6 is also referred to as caudocranial. Such a display prevents the recording of the image of the patient 5 from taking place in the wrong direction, which results in a repetition of the recording. Other symbols 24 can naturally also be used as arrows to display the recording direction. Furthermore, a corresponding symbol 24 can be projected both together with a figure according to a schematic representation 25 of a human body and also as an individual figure on the patient couch 6. Furthermore, various figures and symbols 24 can be projected both overlapping and also separately adjacent to one another on the patient couch 6.

Figure 7:
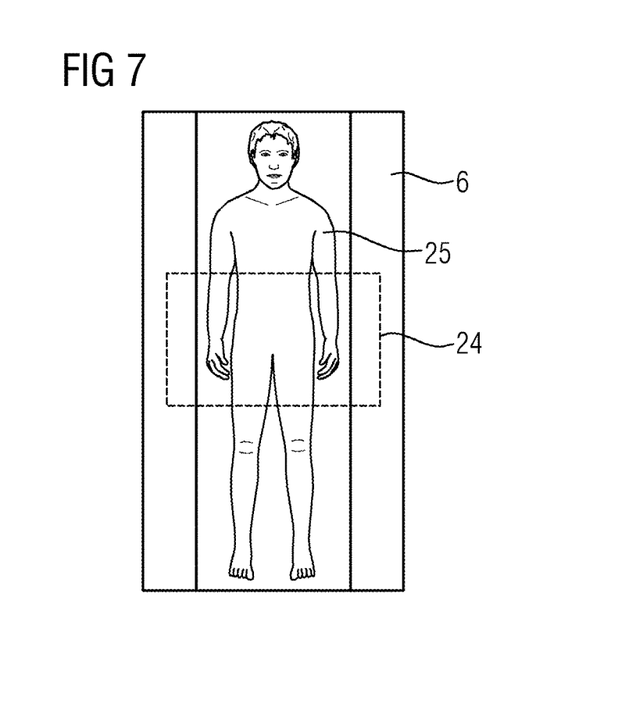
FIG. 7 shows an example projection of a figure specifying the recording area.
Figure 8:
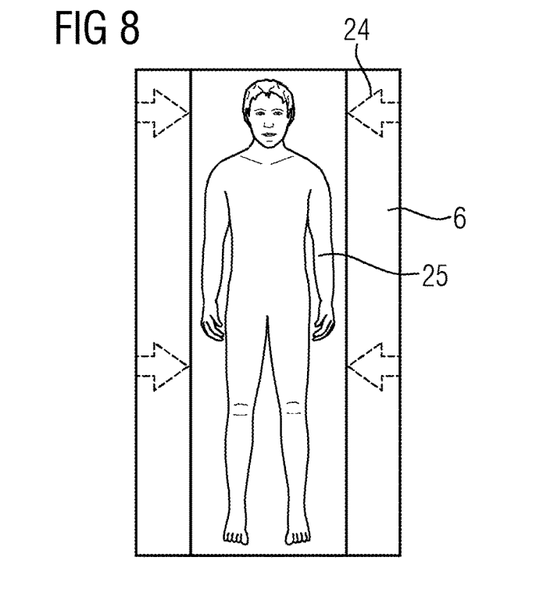
FIG. 8 shows an example projection of a figure specifying the recording area.

FIG. 7 and FIG. 8 show in each instance an example projection of a figure specifying the recording area. Whereas in the example shown in FIG. 7, the recording area is projected as a rectangular surface, in the example shown in FIG. 8, the recording area is bordered by four arrows. A number of recording areas can also be projected for a patient 6. This can be meaningful for instance if a recording of both the knee joint and also the shoulder area is required.

Furthermore, all of the embodiments shown here can be combined with an automatic control of the brightness of the projected area. In particular, exposure to the eyes of the patient 5 of such a bright projection should be prevented as this is unpleasant for the patient 5 or may even cause damage to the eyes of the patient 5. In one embodiment of the invention, the positioning unit is configured such that the area of the projection, at which the eyes of the patient 5 are to be positioned, is illuminated less brightly than adjacent areas of the projection. In particular, the area of the projection, at which the eyes of the patient 5 are to be positioned, can be illumined less brightly than all other areas of the projection or not illuminated at all. The control unit 22 can either obtain the information relating to the positioning of the eyes of the patient 5 directly from the patient data 12 or can calculate the same with the aid of the protocol 10 and/or the patient data 12.

In further embodiments of the invention, the positioning unit has a camera for recording images of the patient 5 in the visible spectral range. Such a camera is for instance a conventional video camera. The camera is connected to the control unit 22 such that it is possible for the control unit 22 to calculate the current position of the eyes of the patient 5 from the images recorded by the camera and accordingly to effect a less bright illumination of the area where the eyes of the patient 5 are currently located. The control unit 22 or a separate program interacting with the control unit 22 can be designed for the automatic recognition of the eyes of a patient 5 in the images of the camera, in particular by methods of image processing such as filtering, segmentation and pattern recognition.

Figure 9:
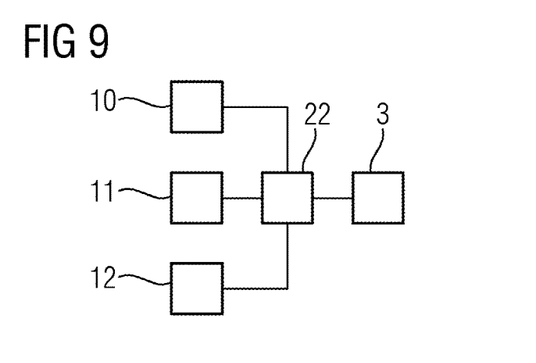
FIG. 9 shows an example and schematic representation of the interaction between various elements of an embodiment of the invention.

FIG. 9 shows by way of example and schematically the interaction of various elements of at least one embodiment of the invention. The technical effect of at least one embodiment of the invention relates on the one hand to the improvement in the positioning of a patient 5 for the recording of an image, in particular a tomographic image. By projecting the positioning aid according to the invention, a positioning is enabled such that a recording can be implemented in a particularly efficient fashion. As already discussed, the whole recording process is accelerated and the susceptibility to error is lowered.

The technical effect further relates to improving the positioning of a patient 5 as a function of a protocol 10, in particular a positioning takes place with at least one embodiment of the inventive positioning unit. A functional relationship is then developed between the recording parameters stored in the protocol 10 and the projection of a positioning aid. This functional relationship is lost in the further variants of the invention; for instance if a symbol 24 for displaying the direction of the recording is projected. Further functional relationships also arise if the projected figure is based on a scalable model 11. In this way properties of the patient 5 can be related to recording parameters of the protocol 10 such that an even quicker and less error-prone positioning of the patient 5 is enabled. With this in mind, the positioning unit with the control unit 22 and the imaging device 7 with such a positioning unit are also quicker and less prone to error.

Figure 10:
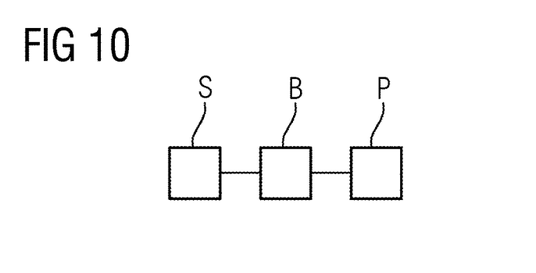
FIG. 10 shows a flow chart of a method for optically generating a positioning aid.

FIG. 10 shows a flow diagram of a method for optically generating a positioning aid. FIG. 10 shows how the individual steps for the optical generation of a positioning aid can be implemented by way of at least one embodiment of an inventive positioning aid. The previously explained technical effects and functional relationships extend according to the respective embodiment also to the method shown here. In this way the method can be varied so that it corresponds to the actual embodiment of the invention. The embodiment of the invention shown here thus includes the steps of scaling S a model 11 and calculating B a control signal 1 and finally projecting P a figure as a positioning aid. In the instance shown here, the figure is based on the scalable model 11.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for the optical generation of a positioning aid, comprising:
    projecting an image of a human body figure as a positioning aid in a planar fashion onto a surface of a patient couch, the figure for positioning a patient being suited to record an image of the patient, wherein the figure is projected in a planar fashion onto the patient couch as a function of a protocol for the recording, and wherein the figure is projected in a planar fashion onto the patient couch according to a schematic representation of a human body in a support position.

2. The method of claim 1, wherein the figurative properties of the positioning aid are based on a scalable model.

3. The method of claim 1, wherein a first symbol for displaying the direction of the recording is projected in a planar fashion onto the patient couch.

4. The method of claim 1, wherein a second symbol for displaying the recording area is projected in a planar fashion onto the patient couch.

5. The method of claim 1, wherein the projection takes place via a projector, the projector being disposed centrally above the patient couch.

6. The method of claim 1, wherein the position of the patient couch and the figure are controlled so as to project the figure at a specific position relative to the patient couch.

7. The method of claim 1, further comprising:
    obtaining, via a processor, stored patient data;
    obtaining, via the processor, parameter values for a scalable model from the obtained data; and
    creating, via the processor, a planar projection based on the obtained patient data.

8. The method of claim 1, further comprising controlling a position of the patient couch relative to a desired location of the projection onto the patient couch.

9. The method of claim 1, further comprising projecting a symbol indicating a scan direction of a recording.

10. The method of claim 1, further comprising overlaying a projected symbol on the projected schematic representation of a human body figure.

11. A non-transitory computer readable medium, including a plurality of computer segments which, when executed on a computer device, implement the method of claim 1.

* * * * *

UNITED STATES PATENT AND TRADEMARK OFFICE
CERTIFICATE OF CORRECTION

PATENT NO. : 10,376,217 B2  
APPLICATION NO. : 14/661502  
DATED : August 13, 2019  
INVENTOR(S) : Bernhard Schmidt and Martin Sedlmair

Page 1 of 1

It is certified that error appears in the above-identified patent and that said Letters Patent is hereby corrected as shown below:

On the Title Page

Item (54) Title and in the Specification Column 1 Lines 1-4 should read as follows:
POSITIONING UNIT FOR POSITIONING A PATIENT, IMAGING DEVICE AND METHOD FOR THE OPTICAL GENERATION OF A POSITIONING AID Signed and Sealed this
Twenty-first Day of April, 2020

Andrei Iancu
*Director of the United States Patent and Trademark Office*